United States Patent
Olson et al.

(10) Patent No.: US 9,723,843 B2
(45) Date of Patent: Aug. 8, 2017

(54) FAMILY OF SILVER (I) PERIODATE COMPOUNDS HAVING BROAD MICROBIAL PROPERTIES

(71) Applicant: Innovotech, Inc., Edmonton (CA)

(72) Inventors: Merle E. Olson, Calgary (CA); Patricia Nadworny, Sherwood Park (CA); Amin M Omar, Edmonton (CA); Yanira E Cabrera, Edmonton (CA)

(73) Assignee: INNOVOTECH INC., Edmonton (CA)

( * ) Notice: Subject to any disclaimer, the term of this patent is extended or adjusted under 35 U.S.C. 154(b) by 0 days.

(21) Appl. No.: 15/003,753

(22) Filed: Jan. 21, 2016

(65) Prior Publication Data

US 2016/0135469 A1 May 19, 2016

Related U.S. Application Data

(63) Continuation of application No. 14/240,733, filed as application No. PCT/CA2012/000796 on Aug. 22, 2012, now abandoned.

(60) Provisional application No. 61/525,920, filed on Aug. 22, 2011.

(51) Int. Cl.
| | | |
|---|---|---|
| *A01N 59/16* | (2006.01) | |
| *A61L 15/18* | (2006.01) | |
| *A61L 15/42* | (2006.01) | |
| *C09D 5/14* | (2006.01) | |
| *A01N 25/08* | (2006.01) | |
| *A01N 59/12* | (2006.01) | |
| *A61L 15/44* | (2006.01) | |

(52) U.S. Cl.
CPC ............. *A01N 59/16* (2013.01); *A01N 25/08* (2013.01); *A01N 59/12* (2013.01); *A61L 15/18* (2013.01); *A61L 15/42* (2013.01); *A61L 15/44* (2013.01); *C09D 5/14* (2013.01)

(58) Field of Classification Search
CPC ........ A01N 59/12; A01N 59/16; A01N 25/00; A01N 25/34; A01N 25/08; A61L 15/18; A61L 15/42; A61L 15/44; C09D 5/14
See application file for complete search history.

(56) References Cited

U.S. PATENT DOCUMENTS

| | | | | |
|---|---|---|---|---|
| 6,355,858 B1 * | 3/2002 | Gibbins | ................. | A61L 15/22 602/41 |
| 6,605,751 B1 * | 8/2003 | Gibbins | ................. | A61K 9/70 602/41 |
| 2001/0055622 A1 * | 12/2001 | Burrell | ................. | A61K 33/24 424/600 |
| 2010/0129466 A1 * | 5/2010 | Marques | ................ | A01N 59/16 424/618 |

OTHER PUBLICATIONS

Roscoe (A Treatise on Chemistry. 1920; vol. 1: pp. 371-372).*
Wan et al. (materials and Design. 2008;29:2034-2037).*
Lockyer (Nature. 1893; vol. 47;p. 84).*
Temme (J Chem Soc 1972,68,350-356).*
Arend (Abstract of: Materials Research Bulletin 1971; 2 pages).*

* cited by examiner

*Primary Examiner* — Ernst V Arnold
(74) *Attorney, Agent, or Firm* — The Law Office of William J. Bundren

(57) ABSTRACT

The present invention is silver (I) periodate compounds and their use in preventing or reducing microbial contamination. The invention includes coatings and articles of manufacture having a surface containing an anti-microbial silver (I) compound. Methods of treatment are also disclosed.

15 Claims, No Drawings

FAMILY OF SILVER (I) PERIODATE COMPOUNDS HAVING BROAD MICROBIAL PROPERTIES

I. FIELD OF THE INVENTION

This invention relates to silver iodate compounds, such as silver (I) periodates, and their use in preventing or reducing microbial contamination. The compositions and methods are suitable for treating or preventing microbial contamination on any surface, particularly metals; polymers and plastics; organic surfaces, such as cotton fibers; and plants, including seeds and leaves. The compounds of the present invention may be formed with a substrate or substrate ingredient or may be a layer on a substrate.

This invention also relates to antimicrobial compositions and the use of these compositions with various devices, preferably devices such as medical devices, in which having an antimicrobial property is beneficial.

The invention also relates to articles produced or formed using the antimicrobial compounds and compositions of the present invention. For example, these compositions may be used in the making of or coating of articles, such as medical devices.

The invention also relates to coatings and/or ingredients in the manufacture of devices where having an antimicrobial property is beneficial, e.g., a medical device or an implant.

II. BACKGROUND OF THE INVENTION

Silver is known for its antimicrobial properties, particularly when incorporated into or onto medical devices. However, it is challenging to coat or incorporate silver onto a surface, whether medical device or other surfaces (e.g., seeds, plants, metals, etc.). Many products formed using existing silver compounds are poorly soluble, exhibit poor silver release profiles, the silver is inactivated in body fluids, and the anti-microbial activity is designed for planktonic bacteria and show little or no effect against biofilm.

One conventional approach for obtaining antimicrobial medical devices is the deposition of metallic silver directly onto the surface of the substrate (for example, by vapor coating, sputter coating, or ion beam coating). However, these noncontact deposition coating techniques suffer many drawbacks, including poor adhesion, lack of coating uniformity, and the need for special processing conditions, such as preparation in darkness due to the light sensitivity of some silver salts. One particular drawback of these coatings is that the processes by which the coatings are formed do not adequately coat hidden or enclosed areas, such as the interior lumen of a catheter or stent. Additionally, these methods produce coatings that are very much like metallic silver in that they do not release silver from the coating and require contact with the coating to provide antimicrobial action. Because they do not release sufficient silver ions into aqueous fluids, they offer little or no protection from bacteria carried into the body upon application of the device and do not inhibit infection in the surrounding tissue or fluid.

Another method of coating silver onto a substrate involves deposition or electrodeposition of silver from solution. Drawbacks of previous deposition methods include poor adhesion, low silver pick-up on the substrate, complex manufacturing processes, the need for surface preparation, high labor costs, and the need for additional deposition agents and stabilizing agents.

Some silver coatings release, to varying degrees, silver ions into the solution or tissue surrounding the substrate. However, activation of such coatings often requires conditions that are not suitable for use with some medical implants. These conditions include abrasion of the coating surface, heating to a temperature above 180° C., contact with hydrogen peroxide, and treatment with an electric current.

Another conventional approach for obtaining antimicrobial medical devices is the incorporation of silver, silver salts, and other antimicrobial compounds into the polymeric substrate material from which the article is formed. An antimicrobial metal may be physically incorporated into the polymeric substrate in a variety of ways. For example, a liquid solution of a silver salt may be dipped, sprayed, or brushed onto the solid polymer, for example, in pellet form, prior to formation of the polymeric article. Alternatively, a solid form of the silver salt can be mixed with a finely divided or liquefied polymeric resin, which is then molded into the article. Further, the antimicrobial compound can be mixed with monomers of the material prior to polymerization.

There are several disadvantages to this approach. One such disadvantage is that larger quantities of the antimicrobial material are required to provide effective antimicrobial activity at the surface of the device. A second disadvantage is that it is difficult to produce articles that actually release the antimicrobial ions because most device polymers absorb little, if any, water to aid in the diffusion and release of the antimicrobial ions, resulting in articles that provide only a limited antimicrobial effect.

To the knowledge of the inventors, $Ag_5IO_6$ has only been used in the context of developing new electrochemical cells, and its antimicrobial properties have not been previously investigated in the published literature. There is a continuing need for active agents that can be incorporated into articles while retaining antimicrobial activity. Further, there is a need for coating compositions that exhibit improved adhesion.

There is also a need for compositions that overcome the solubility, settling, and agglomeration problems of conventional antimicrobial compositions, and exhibit enhanced, sustained release of antimicrobial agents. There is also a need for antimicrobial compositions that may be incorporated into a polymer used to make or coat a device, while retaining its antimicrobial effectiveness. There is also a need for antimicrobial compositions that are stable, e.g., thermally stable, light stable, stable in the materials they are included on/with, and are not inactivated in the environment of their intended use.

III. SUMMARY OF THE INVENTION

The compositions and methods of the present invention comprise one or more silver iodate compounds and their use as antimicrobial agents. The invention also includes articles of manufacture that include one or more of these compounds as a layer or coating on the article.

The compositions and methods of the present invention have applicability in a wide variety of agricultural, industrial, and medical environments, e.g., disinfecting any surface, particularly disinfecting work or processing surfaces (e.g., tables); in antimicrobial coatings; in medical devices and implants, particularly where having an antimicrobial property or characteristic would be beneficial; and in treating human, plant, and animal diseases and conditions.

The compositions and methods of the present invention are also effective in treating and/or eradicating biofilm.

The active agents of the present invention, and in particular, articles coated with these active agents, are an improvement over what is commercially available. The examples show better activity on wound dressings than commercially available silver-containing dressings, particularly after exposure to bodily fluids (saline/human serum).

The active agents of the present invention are a family of silver (I) periodates having a high oxidation state iodine and an oxidized silver ion, e.g. $Ag_5IO_6$. The inventors believe that the iodine facilitates silver transfer, in a form such as $[Ag_2IO_6]^{3-}$, through the biofilm structure or matrix. The inventors also believe that the silver ions, which are present in both the cation ($[Ag_3]^{3+}$) and the anion ($[Ag_2IO_6]^{3-}$), and iodine ions provide multiple antimicrobial methods of action, thus providing improved antimicrobial activity as compared to conventional compounds.

Some of the active agents of the present invention have a small grain size, exhibit polycrystallinity, and have a surface area that, in combination, results in greater anti-microbial activity.

IV. DETAILED DESCRIPTION OF THE INVENTION

The present invention involves silver iodate compounds, such as silver (I) periodates, and their use as antimicrobial agents. Some embodiments of the invention include one or more silver iodate compounds as an active agent(s) imparting an antimicrobial property or properties. The present invention also involves the use of one or more of these active agents to impart an antimicrobial property or properties to a polymer, metal, plastic, or organic surface.

In accordance with the present invention, the active agent includes a family of silver (I) periodate compounds. All of the members of the family are silver (I) combined with a higher oxidation state iodine and coordinated with oxygen atoms. These compounds include but are not limited to silver (I) iodate; pentasilver hexaoxoiodate; $Ag_5IO_6$; silver orthoperiodate; silver periodate (VII); silver iodate (VII); 5 $Ag_2O.I_2O_7$; $Ag_2H_3IO_6$; $Ag_xH_yIO_6$, where x+y=5; $Ag_x$-$M_yIO_6$, where the total cationic charge of x+y=5 and M is one or more cations; and combinations thereof. In preferred embodiments of the invention, the cation may be selected from the group consisting of K, Na, Mg, Ca, Au, Pt, Cu, and Fe. The most preferred cations are potassium and sodium.

The compounds of the present invention may be used by themselves, may be an ingredient in a composition, or may be a part or element of an article of manufacture (e.g., a wound dressing, a medical grade metal, or a catheter). The compounds of the present invention may be combined with and/or formulated into a composition.

Some embodiments of the invention include one or more diperiodatoargentate reaction products that form in an aqueous solution. In preferred embodiments, the reaction products are formed in a hydrothermal reaction.

Any of the active agents of the present invention may be used to impart antimicrobial properties to a surface or a substrate. For example, one or more active agents may be incorporated into the structure of substrate or as a coating or the like. Exemplary substrates include metals, wound dressings, medical devices and instruments; and plants, including seeds and leaves.

The silver (I) periodate family of compounds of the present invention may be produced or synthesized by following processes already known to those skilled in the art. Examples of these processes include:

(1) Kovalevskiy, A., and Jansen, M. Synthesis, Crystal Structure Determination, and Physical Properties of $Ag_5IO_6$. Z Anorg Allg Chem 2006; 632:577-581.

(2) Cignini, P., Icovi, M., Panero, S., and Pistoia, G. On the possibility of using silver salts other than $Ag_2CrO_4$ in organic lithium cells. J Power Source 1978; 3:347-357.

(3) Chapter 9. Oxysalts of Iodine. In: High Temperature Properties and Thermal Decomposition of Inorganic Salts. ©2001, CRC Press LLC.

(4) Mackay, Mackay, and Henderson. Introduction to modern inorganic chemistry, pg. 489.

(5) Gyani, P. Periodic Acid and Periodates. II The system silver oxide-periodic acid-water at 35° C. J Phys Chem 1951; 55(7):1111-1119.

(6) International Patent Application No. PCT/CA2011/000941, filed 22 Aug. 2011, incorporated herein by reference in its entirety.

The present invention also includes methods of coating a surface or a substrate with an active agent of the present invention, said methods resulting in imparting an antimicrobial characteristic to the substrate. The present invention also includes methods of coating a wound dressing substrate with an active agent of the present invention, said methods resulting in imparting an antimicrobial characteristic to the substrate. As used herein, wound dressing substrate includes but is not limited to a wide variety of wound dressing substrates, including polymer-based substrates such as high density polyethylene and polyester, and organic based substrates such as cotton and rayon.

The compositions and methods may also include one or more other active agents.

In some embodiments of the invention, one or more silver (I) periodate compounds are used to produce an article having improved antimicrobial characteristics. In some of these embodiments of the invention, the silver (I) periodate compound may be a coating or the like on a surface of the article, or may be incorporated into a material that forms the article. In some embodiments of the invention, the article comprises titanium or stainless steel. In some embodiments of the invention, the article is a medical device, such as a catheter, wound dressing, or needle. Some embodiments of the invention include forming an article including an active agent of the present invention, thereby forming an article having one or more antimicrobial properties.

For one or more the active agents of the present invention, the small grain size and the larger particle size contribute to enhanced or improved anti-microbial activity. For example, $Ag_5IO_6$ has a particle size of about 15 Å (fifteen angstroms), that is, nano size, and a particle size that is much larger (typically between about 2 and 20 μm, that is, not nano). The grain size may increase with some forms of processing or post-synthesis processing, e.g., heating, exposure to solutions, grains growing together, grains combining into a single larger grain, and the like.

Some embodiments of the invention include a coating, layer, or the like on an article, said coating, etc., comprising one or more active agents of the present invention, and imparting improved antimicrobial characteristics to the article or a portion of the article.

In some embodiments of the invention, the composition may be any form that does not inactivate the silver, including but not limited to a gel, ointment, cream, foam, or ingredient or layer in a polymer, substrate, or carrier.

In some embodiments of the invention, the active agent or a composition containing the active agent may be any form that does not inactivate the silver, including but not limited to a layer; or ingredient in a metal, polymer, or organic material; or a carrier. The preferred forms are a silver (I) periodate powder, or a coating that includes a silver (I) periodate.

In some embodiments of the invention, the compositions and methods are used for treating a microbial contaminant using an antimicrobial agent comprising silver ions or silver-containing complexes. The compositions and methods may also include one or more other active agents. The compositions and methods are antimicrobial, e.g. against biofilm, similar structures, or precursors formed by bacteria, fungi, viruses, algae, parasites, yeast, and other microbes. A microbial contaminant or infection may be found in a variety of species, including but not limited to humans, pigs, ruminants, horses, dogs, cats, plants, and poultry.

In some embodiments of the invention, the active agent(s) may be incorporated into or onto packaging for an article, such as a medical device or a needle.

In some embodiments of the invention, one or more active agents or one or more starting materials may be used for the manufacture of a medicament intended to treat or prevent infections or contamination, particularly infections caused by bacteria, bacteria-like organisms, fungi, yeast, or biofilms.

The silver compositions of the present invention may be used with or incorporated into an article where antimicrobial properties are desirable and/or beneficial. Examples include, but are not limited to, medical and surgical devices and/or environments, such as implants. Other examples are provided below.

The silver compositions of the present invention may be used to coat, or may be incorporated into, any article comprising a metal or metal alloy. Typical metals and alloys include, but are not limited to titanium, titanium containing alloys, aluminum, stainless steel, mild steel, and copper. In preferred embodiments of the invention, the metal is titanium (grade 2), titanium (grade 5), aluminum, stainless steel, stainless steel needles, titanium (grade 5) pins, and other titanium (grade 5) implants.

The silver compositions of the present invention may be used to coat, or may be incorporated into, any article comprising a wound dressing. Typical wound dressings include polymeric and organic-based wound dressings.

In another embodiment, the composition optionally contains additional antimicrobial metals or salts of these antimicrobial metals, such as zinc, gold, copper, cerium, and the like. In yet another embodiment, the composition optionally comprises additional noble metals or salts of one or more noble metals to promote galvanic action. In still another embodiment, the composition optionally comprises additional platinum group metals or salts of platinum group metals such as platinum, palladium, rhodium, iridium, ruthenium, osmium, and the like.

In some embodiments, the compositions optionally contain other components that provide beneficial properties to the composition, that improve the antimicrobial effectiveness of the composition, or that otherwise serve as active agents to impart additional properties to the composition. The compositions are also used to inhibit algal, fungal, mollusk, or microbial growth on surfaces. The compositions of the invention are also used as herbicides, insecticides, antifogging agents, diagnostic agents, screening agents, and antifoulants.

In another embodiment, the composition may be applied as a coating to a preformed article, part of an article, a plant or portion thereof (e.g., a seed or a leaf), or a substrate. The coating may be produced, for example, by dipping the article, etc., into the composition or by spraying the article with the composition and then drying the coated article.

Some embodiments of the present invention include providing compositions that provide antimicrobial, antibacterial, antiviral, antifungal, anti-biofilm, or antibiotic activity, or some combination thereof.

Some embodiments of the present invention include providing compositions that reduce encrustation, inhibit coagulation, improve healing, inhibit restenosis, or impart antiviral, antifungal, antithrombogenic, or other properties to coated substrates.

Some embodiments of the present invention include providing compositions that inhibit the growth of algae, mollusks, bacteria, bioslime, or some combination thereof on surfaces.

As described in more detail below, the methods and compositions of the present invention may be used wherever biofilm or similar structures may be found, including but not limited to microorganisms growing and/or floating in liquid environments. The antimicrobial or anti-biofilm effect may be biostatic or biocidal.

In some embodiments of the invention, the compositions and methods may be used to treat or prevent one or more biofilms. In some embodiments of the invention, the compositions and methods may be used to treat and/or prevent one or more human, animal, or plant diseases, conditions, infections, or contaminations. Typically these diseases and infections, etc., are caused by microbes associated with or residing in the biofilm.

The present invention includes any method of contacting with an antimicrobial agent of the present invention. Typical mechanisms of contacting include, but are not limited to, coating, spraying, immersing, wiping, and diffusing in liquid, powder, or other delivery forms (e.g., injection, tablets, washing, vacuum, or oral). In some embodiments of the invention, the compositions and methods may include applying the active agent to any portion of an article or an ingredient of an article.

The Examples provide experimental confirmation that the silver (I) periodate compounds of the present invention release silver over time, typically over fourteen or more days. These Examples therefore demonstrate that stable, slow release silver-containing compounds can be used as long-lasting antimicrobials against bacterial and fungal pathogens, including biofilms growing on a substrate or layer.

These compositions exhibit antimicrobial activity and/or anti-biofilm activity against a variety of microbes, including both bacteria and fungi, and provide a sustained release of silver ions or silver containing complexes from silver compounds.

The preferred composition of the present invention comprises an active agent that results in an ionic silver species or silver-containing complex. Silver complexes or compounds, as used herein, refers to a composition containing silver having a valent state of one or higher, such as, for example Ag(I), Ag(II), and Ag(III) valent states. The compositions and methods of the invention may be comprised of silver ions, complexes, or compounds having more than one valent state so that the oxidized silver species may be comprised of a multivalent substance. Finally, the compositions of the present invention may be comprised of a silver-containing substance or a plurality of silver containing substances that may react over time to form other silver containing substances which may exhibit differing antimicrobial properties.

In preferred embodiments of the invention, antimicrobial properties may be achieved by contacting an antimicrobially active silver species within or at the surface of a substrate, or diffusing from the surface of a substrate into an aqueous environment.

The silver compounds may be used in any of the following formats: silver deposition coatings, liquid, suspension, powder, capsule, tablet, coating, incorporation, and similar configurations. In a preferred embodiment of the present invention, active agents are incorporated directly onto or into a material, or may be incorporated by sequentially adding components or precursors of the active agent to the material, and having the precursors of the active agent in or on the coating. Other forms also include films, sheets, fibers, sprays, and gels.

Examples of additional antimicrobial agents are known to those skilled in the art and include, but are not limited to: streptomycin, tetracycline, erythromycin, ciprofloxacin, doxycycline, ampicillin, penicillin, gentamicin, and heavy metals including, but not limited to, gold, platinum, silver, zinc, and copper, and their combined forms including salts, such as chloride, bromide, iodide, nitrate, sulphate, and periodate, complexes with carriers, and other forms.

Multiple inactive ingredients may be optionally incorporated in the formulations. Examples of such ingredients are emulsifiers, thickening agents, solvents, anti-foaming agents, preservatives, fragrances, coloring agents, emollients, fillers, and the like.

The compositions and methods of the present invention may be used to treat planktonic microorganisms and/or biofilm in a wide range of environments and places. Treating biofilm, as used herein, refers to contacting a biofilm or similar structure with an anti-biofilm agent wherever biofilm may be found, is expected to be found, or is postulated to be found. One skilled in the art will readily recognize that the areas and industries for which the present invention is applicable include a vast number of processes, products, and places.

The active agent(s) incorporated into the matrices and devices of the present invention may be used for a variety of applications where there is a need for or benefit from the presence of the active agent.

In this aspect of the invention, the compositions and methods are suitable for treating against one or more microbial infections, including but not limited to diseases or conditions caused by *Pseudomonas aeruginosa, Staphylococcus aureus, Klebsiella pneumoniae, Clostridium difficile, Candida albicans, Staphylococcus epidermidis, Escherichia coli, Streptococcus* spp, Pseudomonads, Xanthomonads, and *Curtobacterium* species.

The active agents of the present invention may also be used to treat plant pathogens, including but not limited to *Pseudomonas syringae* pv. *syringae, Pseudomonas syringae* pv. *phaseolicola*, and *Curtobacterium flaccumfaciens* pv. *flaccumfaciens*.

The compositions may be used to coat substrate materials. Thus, another aspect of the invention is a coating containing the composition of the invention. These coatings may comprise either a single layer or multiple layers. The compositions of the present invention are used alone or in combination with polymer coatings to provide advantageous properties to the surface of the substrate. These compositions are used, for example, to deliver pharmaceutical agents that, for example, prevent infection, reduce encrustation, inhibit coagulation, improve healing, inhibit restenosis, or impart antiviral, antifungal, antithrombogenic, or other properties to coated substrates.

The compounds of the present invention and/or their reaction products may be incorporated into any wound dressing, bandage, or wound healing product.

The active agents of the present invention also exhibit good storage stability. As shown in the Examples, $Ag_5IO_6$ powder is stable at 90° C. for >28 days, which correlates to stability for greater than two years at room temperature.

The active agents of the present invention also exhibit good photostability. As shown in the Examples, $Ag_5IO_6$ powder is photostable, and therefore does not need to be stored in the absence of light.

The active agents of the present invention are also thermally stable. As shown in the Examples, $Ag_5IO_6$ powder is stable up to 440° C., indicating that the active agents of the present invention may be used under the high heat thermal processing required in the manufacture of some medical devices.

The active agents of the present invention may also be formulated into a composition comprising a solvent with short term stability. Exemplary solvents include, but are not limited to, water, saline (where some initial breakdown occurs but appears to be self-limited), methanol, acetone, acetonitrile, and tetrahydrofuran.

The active agents of the present invention exhibit improved and commercially valuable antimicrobial activity and longevity. As shown in the Examples, silver(I) periodate exhibits bacteriostatic longevity on wound dressings for greater than 10 days in vitro using day-to-day transfer corrected zone of inhibition testing, and bactericidal longevity on wound dressings greater than 14 days in vitro with continuous exposure to saline followed by a challenge in human serum and media in saline.

The active agents of the present invention also exhibit broad range antimicrobial activity. As shown in the Examples, would dressings coated with an active agent of the present invention are antimicrobial against fungi, bacteria (Gram-positive and Gram-negative pathogens, including *C. difficile*), both against planktonic forms and as anti-adherent/anti-biofilm agents. Further, these active agents retain their antimicrobial activity in environments that reduce or eliminate the antimicrobial effect of some silver species, e.g., in the presence of bodily fluids such as human serum and physiological saline.

The active agents of the present invention may be used in the agricultural industry as an antimicrobial agent or composition. As shown in the Examples, one or more agents are suitable for use as an antimicrobial seed coating or in a foliar spray. Agents have demonstrated bactericidal activity (anti-adherence and anti-planktonic) against plant pathogens, including after exposure to soil.

Definitions

The following definitions are used in reference to the invention:

As used herein, active agent describes a silver-containing chemical substance, compound, or complex that exhibits antimicrobial activity, and is Ag (I) combined with a higher oxidation state iodine and coordinated with oxygen atoms. Active agent includes but is not limited to a silver(I) periodate; one or more reaction products of a sodium diperiodatoargentate, each of these reaction products containing iodine; one or more reaction products of a potassium diperiodatoargentate, each of these reaction products containing iodine; pentasilver hexaoxoiodate; $Ag_5IO_6$; silver orthoperiodate; silver periodate (VII); silver iodate (VII); 5 $Ag_2O \cdot I_2O_7$; $Ag_2H_3IO_6$; and other combinations of $Ag_xH_yIO_6$ where x+y=5; $Ag_xM_yIO_6$, where the total cationic charge of x+y=5 and M is one or more cations; and combinations thereof. One skilled in the art will readily recognize that the cation can be any of a large number of cations. Exemplary cations include but are not limited to K, Na, Mg, Ca, Au, Pt, Cu, and Fe. The preferred cations are K and Na. Active agent also includes compositions comprising one or more active agents.

Reaction product, as used herein, refers to any silver containing compound or complex in the silver iodate family, formed by a number of different reaction processes. Exemplary reaction products include but are not limited to pentasilver hexaoxoiodate; $Ag_5IO_6$; silver orthoperiodate; silver periodate (VII); silver iodate (VII); $5 Ag_2O.I_2O_7$; $Ag_2H_3IO_6$; and other combinations of $Ag_xH_yIO_6$ where x+y=5, $Ag_xM_yIO_6$, where the total cationic charge of x+y=5 and M is one or more cations (including those specified above); and combinations thereof. All of the starting materials form at least one compound or complex that releases silver having a valence of 0, 1, 2, 3, or higher.

As used herein, antimicrobial includes antibacterial, including planktonic or biofilm forms. A preferred antimicrobial compound or composition is also anti-biofilm. Anti-biofilm agent refers to any element, chemical, biochemical, or the like that is effective against a biofilm. Typical anti-biofilm agents are those that have antimicrobial, antibacterial, anti-fungal or anti-algal properties. Metal and metal compounds, preferably ionic silver-containing species, have been shown generally to have antibacterial and ethylene inhibiting properties, and are preferred anti-biofilm agents in accordance with the present invention. In some embodiments of the invention, the anti-biofilm agent is a broad spectrum agent, e.g., having effectiveness or activity against more than one microbial species.

"Sustained release" or "sustainable basis" are used to define release of atoms, molecules, ions, or clusters of a noble metal that continues over time measured in hours or days, and thus distinguishes release of such metal species from the bulk metal, which release such species at a rate and concentration which is too low to be effective, and from highly soluble salts of noble metals such as silver nitrate, which releases silver ions virtually instantly, but not continuously, in contact with an alcohol, aqueous solution, or electrolyte. The active agents of the present invention are superior to other commercially available silver containing compounds in part because of the slow release of silver.

Medical device as used herein refers to any device, tool, instrument implant, or the like, relating to medicine or the practice of human or veterinary medicine, or intended for use to heal or treat a disease or condition. A medical device of the present invention may be used for the medical benefit of a human or animal, including laboratory or hospital equipment. A medical device or a component of a medical device may include all natural and synthetic materials and both fibrous and non-fibrous materials. For example, the materials may be comprised of a metal, plastic, paper, glass, ceramic, textile, rubber, polymer, composite material or any other material or combination of materials. Exemplary medical devices include, but are not limited to, catheters; cannulae; needles; stents; guide wires; implant devices; filters; endoscopes; surgical or medical instruments; stents of any size, shape, or placement; coils of any size, shape, or placement; contact lenses; IUDs; peristaltic pump chambers; endotracheal tubes; gastroenteric feeding tubes; arteriovenous shunts; condoms; oxygenator and kidney membranes; gloves; pacemaker leads; wound dressings; metallic pins, plates, and screws; metallic artificial hips; artificial knees; and gels, creams, and ointments. Surface contamination, as used herein, refers to microorganisms growing on or relocated to a surface. The microorganisms associated with surface contamination may be actively growing or dormant, but represent a viable inoculum that can reinitiate infection, disease or other undesirable conditions.

Antimicrobial activity is art-recognized and may be biostatic and/or biocidal. Biostatic materials are materials that inhibit the growth of all or some of the microorganism; and a biocide is a material that kills all or some of the microorganism. The active agents of the present invention are sufficiently soluble to provide biostatic and/or biocidal activity.

The term "coating" as used herein generally includes coatings that completely cover a surface, or portion thereof, as well as coatings that may only partially cover a surface, such as those coatings that after drying leave gaps in coverage on a surface. The latter category of coatings may include, but are not limited to a network of covered and uncovered portions (e.g., non-continuous covered regions of the surface). When the coatings described herein are described as being applied to a surface, it is understood that the coatings need not be applied to, or that they need not cover, the entire surface. For instance, the coatings will be considered as being applied to a surface even if they are only applied to modify a portion of the surface. The coating may be applied to a surface or impregnated within the material used to construct an item or a portion of an item.

The term "substrate" as used herein generally refers to a body or base layer or material (e.g., onto which other layers are deposited). A substrate may be organic (e.g., cotton or wool), metal, a polymer (e.g., rayon or polyester), or cellular (e.g., a plant, a seed, leaves, skin, or hide). Metal substrate includes but is not limited to a wide variety of metals (e.g., titanium and stainless steel); metal alloys; and devices or products made using these metals (e.g., medical devices, needles, ports, implants, pins, etc.). In accordance with the present invention, the substrate must not inactivate the silver compound, or inactivate it to the extent that the silver is no longer suitable for use as an anti-microbial agent.

EXAMPLES

Example 1. Coating Grade 2 Titanium with $Ag_5IO_6$

Various hydrothermal reaction methods have been developed with the starting component being sodium diperiodatoargentate in distilled water, which was reacted to coat Grade 2 (commercially pure) titanium with $Ag_5IO_6$:
1) Titanium cord was placed in the reaction vessel during the formation of sodium diperiodatoargentate.
2) Titanium cord was placed in a concentrated solution of sodium diperiodatoargentate, which was then heated at 80° C.
3) Titanium cord was placed in a concentrated solution of sodium diperiodatoargentate, which was then autoclaved.

Titanium (Ti) cords coated using all three methods were tested for bacteriostatic longevity using day-to-day transfer corrected zone of inhibition (CZOI) assays against *Pseudomonas aeruginosa*.

The longevity of method (1) was 3 days, the longevity of method (2) was 8 days, and the longevity of method (3) was 4 days. The uncoated Ti cords did not generate any zone of inhibition.

The quantity of silver coating the Ti cords, as determined by AAS, indicated that about 30 μg $Ag/cm^2$ coated the samples of all three methods.

Silver-coated Ti cords and uncoated Ti cords imaged via SEM showed that Methods (2) and (3) had a number of small flakes as well as some larger crystals coated on the Ti surface, while Method (1) appeared mostly to have large crystals deposited on the Ti surface. The SEM results showed that the coatings were discontinuous. Energy Dispersive X-ray Spectroscopy (EDS) analysis showed that silver, iodine, and oxygen all mapped to the same locations at the crystals deposited at the Ti surfaces.

X-ray Diffraction (XRD) analysis indicated that the silver compound coated onto the Ti was $Ag_5IO_6$.

Example 2

One or more active agents of the present invention were coated on Tegaderm™, Opsite*, and Tensoplast™, all commercially available wound dressings. Tegaderm™ and Opsite* are film dressings (e.g. acrylate polymers/polyurethane polymers, with an adhesive (e.g. acrylic); Tensoplast™ is a cotton/rayon cloth with an elastic adhesive. They were coated by the following methods:
1. Soaked at room temperature with sodium diperiodatoargentate solution.
2. Soaked at 80° C. with sodium diperiodatoargentate solution.
3. Soaked with water, and then soaked at room temperature with sodium diperiodatoargentate solution.
4. Soaked with water, and then soaked at 80° C. with sodium diperiodatoargentate solution.
5. Same as Method 3, except that 0.9% saline was used for the original soak.
6. Same as Method 4, except that 0.9% saline was used for the original soak.

UV-Vis

None of the dressings produced signal patterns matching that of sodium diperiodatoargentate, suggesting that they were not releasing the starting material into solution, and therefore likely were not coated with the starting material. A strong positive signal was observed with the Tensoplast™ at locations that correspond to silver-containing species.AAS Typically there was low uptake of digestible silver by the Opsite* (0.17-2.28 µg/cm$^2$) and Tegaderm™ (0.09-0.95 µg/cm$^2$). Much higher levels were obtained with the Tensoplast™ using Methods 1-4 and 6 (175, 109, 31, 92, and 15 µg/cm$^2$, respectively), but were low for Method 5 (0.79 µg/cm$^2$).

Overall, these results indicated that coated Tensoplast™ contains substantial amounts of silver, with Methods 1 and 2 resulting in the most silver incorporation/coating, followed by Method 4.

CZOI

Anti-microbial activity was similar for the adhesive (wound side) and non adhesive (back side) of the dressings. For the Opsite*, Method 2 generated zones of inhibition for 1 day only, and the remaining methods generated no zones of inhibition. For the Tegaderm™, Methods 2 and 4 generated zones of inhibition for 1 day only, and the remaining methods generated no zones of inhibition. For the Tensoplast™, Method 1 generated zones of inhibition for up to 10 days, Method 2 generated zones of inhibition for 5 days, Method 3 generated zones of inhibition for 2 days, Method 4 generated zones of inhibition for 4 days, Method 5 generated zones of inhibition for 1 day, and Method 6 generated zones of inhibition for 2 days.

Example 3

Dressings were coated with $Ag_5IO_6$ and then were tested for silver species present (XRD), and bacteriostatic longevity (CZOI) testing.

Dressings coated in this study were used for the diabetic pig wound healing example.
Dressings Coated
  Source Gauze Sponges—100% cotton
  3 ply dressings—rayon/polyester core with upper and lower HDPE layers
Coating Method
  The fibers were coated during the synthesis of $Ag_5IO_6$ from sodium diperiodatoargentate (III) (Method A), during direct $Ag_5IO_6$ synthesis (Method B), and by suspending the fibers in an $Ag_5IO_6$ slurry (Method C).
Results
  Of the coating methods, the autoclave method was the least effective—the 3 ply dressings did not coat adequately to generate zones of inhibition (only 48 ppm Ag was digested from 1 in$^2$ samples in 5 mL digest), while the zone size dropped with time for the gauze dressing (1095 ppm Ag was digested from 1 in$^2$ samples in 5 mL digest). The remaining three methods all generated dressings with comparable silver contents (1134-4203 ppm Ag digested from 1 in$^2$ samples in 5 mL digest) that made consistent zone of inhibition sizes for 10 days, at which point the study was ended, indicating excellent bacteriostatic longevity. In all cases, the only silver compound present on the dressings was $Ag_5IO_6$, as determined by XRD.

Example 4

This study tested Tensoplast™ coated via Method C of Example 3.
Dressings Coated
  Tensoplast—rayon/cotton with adhesive
Results
  X-ray diffraction: The only silver compound identified on the Tensoplast was $Ag_5IO_6$.
  Atomic Absorption Spectroscopy: The silver adsorption was 4.97±2.73 mg/cm$^2$. Note: For gauze dressings and 3 ply dressings coated the same way, the silver adsorption was 3.44±0.99 mg/cm$^2$ and 1.43±0.42 mg/cm$^2$, respectively.
  Day-to-Day Transfer Corrected Zone of Inhibition: When challenged with *P. aeruginosa*, the coated Tensoplast continued to produce zones for 10 days with no signs of decreased zone size. The study was ended at 10 days but it appeared that the Tensoplast could continue to produce zones for a substantial period of time.
  Tensoplast can easily be coated with $Ag_5IO_6$, resulting in excellent bacteriostatic longevity.

Example 5

This study compares $Ag_5IO_6$ coated dressings to uncoated control dressings and initial inoculum concentration for their ability to prevent bacterial adherence/biofilm formation.
  Organisms: *P. aeruginosa, S. epidermidis, S. aureus, K. pneumoniae, C. albicans.*
  Inoculum was made up in 10% MHB/SDB in 0.9% saline+25% human serum to determine ability of $Ag_5IO_6$ coatings to act in the presence of human serum and saline. 24 h was allowed for biofilm growth.
Dressings Coated
  Source Gauze Sponges—100% cotton
  3 ply dressings—rayon/polyester core with upper and lower HDPE layers
  Tensoplast—rayon/cotton with adhesive Results

| | Log Reduction | | | | | |
|---|---|---|---|---|---|---|
| | Source Gauze Sponges | | 3 Ply Dressing | | Tensoplast | |
| | LogR (IC) | LogR (C) | LogR (IC) | LogR (C) | LogR (IC) | LogR (C) |
| Staphylococcus aureus ATCC 6538 | 5.55 | 5.85 | 5.55 | 5.35 | 5.55 | 5.52 |
| Pseudomonas aeruginosa ATCC 9027 | 5.30 | 4.29 | 3.61 | 0.47 | 5.86 | 6.73 |
| Klebsiella pneumoniae ATCC 4352 | 4.09 | 5.21 | 5.06 | 6.54 | 5.26 | 5.73 |
| Staphylococcus epidermidis ATCC 35984 | 5.59 | 7.25 | 5.59 | 7.12 | 5.59 | 4.96 |
| Candida albicans ATCC 18804 | 5.20 | 5.67 | 5.20 | 5.39 | 5.20 | 5.62 |

IC = log reduction calculated relative to the inoculum check.
C = log reduction calculated relative to uncoated controls.

All coating methods demonstrated excellent anti-adherence efficacy against all organisms, with the exception that the 3-ply dressing did not demonstrate anti-adherence efficacy against *Pseudomonas aeruginosa* ATCC 9027 when compared to the uncoated controls.

Statistical analyses were performed using one-way ANOVAs with Tukey-Kramer post-testing to compare the anti-adherence activity of the different coated dressings, within each organism, using the uncoated control data for the analysis. For the *Staphylococcus aureus*, *Candida albicans*, and *Klebsiella pneumoniae*, there were no statistically significant differences between the dressings (p=0.7450, p=0.3513, and p=0.4841, respectively). For the *Staphylococcus epidermidis*, there were statistically significant differences between groups (p=0.0101), with the sponge gauze and 3 ply dressings both generating significantly higher log reductions than the Tensoplast (p<0.05 each). However, it should be noted that the Tensoplast still generated a log reduction>4. For the *Pseudomonas aeruginosa*, there were statistically significant differences between groups (p=0.0295), with post testing indicating that the Tensoplast generated significantly higher log reductions than the 3 ply dressing (p<0.05).

Example 6—Biostatic Longevity

This study measured day-to-day transfer corrected zones of inhibition (CZOIs) using various relevant microorganisms against $Ag_5IO_6$ coated materials.
Dressings and Metals Coated
  316 stainless steel
  Grade 5 Ti
  Grade 5 Ti
  Tensoplast™
  3-ply dressing (HDPE exterior layers, rayon/polyester interior)
  100% cotton sponge gauze
Test Methods
  i. Organisms: *P. aeruginosa* ATCC 9027, *S. aureus* ATCC 6538, *K. pneumoniae* ATCC 4352, *S. epidermidis* ATCC 35984, *C. albicans* ATCC 18804
  ii. Methods: Day-to-day transfer CZOIs, with comparison to uncoated controls.

Number of Days that Zones were Generated

| | Corrected Zone of Inhibition (# of Days) | | | | | |
|---|---|---|---|---|---|---|
| | 316 SS (Dir.) | Gr 5 Ti (Dir.) | Gr 5 Ti (Post) | Gauze | 3 ply | Tenso-plast ™ |
| Staphylococcus aureus ATCC 6538 | 0 | 1 | 9-10 | 9 | >10 | >10 |
| Pseudomonas aeruginosa ATCC 9027 | 0 | 1 | 3 | 5 | 9-10 | >10 |
| Klebsiella pneumoniae ATCC 4352 | 0 | 1 | 6 | 9 | >10 | >10 |
| Staphylococcus epidermidis ATCC 35984 | 0 | 1 | 10 | 3 | >10 | >10 |
| Candida albicans ATCC 18804 | 0 | 0 | 3 | 4 | 4 | 4 |

Statistical Analysis for Differences in Zone Size on Each Day
Note: None of the uncoated materials generated zones of inhibitions on any days. *P. aeruginosa*
  Day 1: Post synthesis-coated Gr. 5 Ti coupons had significantly larger zones than direct synthesis-coated Gr. 5 Ti coupons, and 316 stainless steel didn't generate zones. There were no significant differences between zone sizes of coated dressings.
  Day 2: Only post-synthesis coated Gr. 5 Ti coupons still generated zones. Tensoplast™ generated significantly larger zones than the other two dressings.
  Day 3: The Tensoplast™ had significantly larger zones than the 3-ply dressing. The gauze samples did not generate zones but were transferred and made zones again the next day.
  Day 4: There were no significant differences in zone size between the dressings. The post-synthesis-coated Gr. 5 Ti coupons were no longer generating zones.
  Day 5: The Tensoplast™ had significantly larger zones than the gauze.
  Day 6: The Tensoplast™ had significantly larger zones than the 3-ply dressings. The gauze dressings did not generate zones.
  Day 7, Day 8, Day 9, Day 10: There were no significant differences in zone size between Tensoplast™ and the 3-ply dressing. On Day 10, two of the 3-ply dressings did not generate zones, while all Tensoplast™ pieces were still producing zones.
*S. aureus*
  Day 1: There was no significant difference in zone size between the direct synthesis-coated grade 5 Ti and the post synthesis-coated grade 5 Ti, while the 316 stainless steel did not generate zones. The 3-ply dressings generated significantly larger zones than the gauze.
  Day 2: Only the post synthesis-coated grade 5 Ti was still generating zones. The Tensoplast™ generated significantly larger zone sizes compared to the gauze and 3-ply dressings.
  Day 3: The Tensoplast™ generated significantly larger zone sizes than the gauze and 3-ply dressings.
  Day 4: The Tensoplast™ generated significantly larger zone sizes than the gauze dressings.
  Day 5: The Tensoplast™ generated significantly larger zone sizes than the gauze and 3-ply dressings. The 3-ply dressings generated significantly larger zone sizes than the gauze dressings.

Day 6: The Tensoplast™ generated significantly larger zone sizes than the gauze dressings, as did the 3-ply dressings.

Day 7: The Tensoplast™ generated significantly larger zone sizes than the gauze and 3-ply dressings.

Day 8, Day 9: The Tensoplast™ generated significantly larger zone sizes than the gauze and 3-ply dressings. The 3-ply dressings generated significantly larger zones than the gauze dressings.

Day 10: The gauze dressings did not generate zones. The post synthesis-coated Gr. 5 Ti was still generating zones. The Tensoplast™ generated significantly larger zones than the 3-ply dressings.

K. pneumoniae

Day 1: The post synthesis-coated grade 5 Ti generated significantly larger zones than the direct synthesis-coated grade 5 Ti. The direct synthesis-coated 316 stainless steel did not generate any zones of inhibition. There were no significant differences in zone size between coated dressings.

Day 2, Day 3: There were no significant differences in zone size between coated dressings. Only the post synthesis-coated Gr. 5 Ti was still generating zones.

Day 4: The Tensoplast™ and gauze dressings generated significantly larger zones than the 3-ply dressings.

Day 5: The Tensoplast™ generated significantly larger zones than the 3-ply and gauze dressings.

Day 6, Day 7: The Tensoplast™ and 3-ply dressings generated significantly larger zones than the 3-ply dressings. On Day 7, the post synthesis-coated grade 5 Ti stopped producing zones.

Day 8: There were no significant differences in zone size between coated dressings.

Day 9: The Tensoplast™ generated significantly larger zone sizes than the 3-ply and gauze dressings. The 3-ply dressings generated significantly larger zone sizes than the gauze dressings.

Day 10: The Tensoplast™ generated significantly larger zone sizes than the 3-ply dressings. The gauze dressings did not generate zones.

S. epidermidis

Day 1: The post synthesis-coated Gr. 5 Ti generated significantly larger zone sizes than the direct synthesis-coated Gr. 5 Ti. The direct synthesis-coated 316 stainless steel did not generate zones. The Tensoplast™ generated significantly larger zone sizes than the gauze dressings.

Day 2: Only the post synthesis-coated Gr. 5 Ti was still generating zones. There were no significant differences between dressings.

Day 3: The Tensoplast™ generated significantly larger zones than the 3-ply and gauze dressings.

Day 4, Day 5: The Tensoplast™ and 3-ply dressings did not show significant differences in zone size. The gauze dressings did not generate zones.

Day 6: The 3-ply dressings generated significantly larger zone sizes than the Tensoplast™.

Day 7: The Tensoplast™ and 3-ply dressings did not show significant differences in zone size.

Day 8, Day 9: The Tensoplast™ generated significantly larger zones than the 3-ply dressings.

Day 10: The Tensoplast™ generated significantly larger zones than the 3-ply dressings, and the post synthesis-coated Gr. 5 Ti was still generating zones.

C. albicans

Day 1, Day 2: Of the metals, only the post synthesis-coated grade 5 Ti generated zones of inhibition. There were no significant differences between the zone sizes for the coated dressings.

Day 3: There were no significant differences between the zone sizes for the coated dressings. None of the metals generated zones from Day 3 on.

Day 4: There were no significant differences between the zone sizes for the coated dressings.

Day 5: None of the dressings generated zones.

Conclusion

Post synthesis coated dressings (all 3 types) demonstrated substantial bacteriostatic longevity against a wide range of clinically relevant bacteria (gram positive and gram negative pathogens). In some cases, the dressings were still active after 10 days. The dressings were also active against C. albicans, for a shorter time period (4 days).

Example 7—Bacteriostatic Longevity of Dressings Coated at Various Concentrations of Silver (I) Periodate In this study, wound dressings were coated at different concentrations (similar to Example 6, except that the full amount of $Ag_5IO_6$ was used for some dressings, 5× less material was used for others, and a third group was coated using 10× less $Ag_5IO_6$). Day-to-day transfer corrected zone of inhibition testing was performed using the same 5 organisms as Example 6, except that the Pseudomonas aeruginosa used was ATCC 27853.

Dressings Coated
3-Ply Dressings and Tensoplast™.
Number of Days that Zones were Generated

|  | Corrected Zone of Inhibition (# of Days) | | | | | |
| --- | --- | --- | --- | --- | --- | --- |
|  | Full 3-ply | 5× less 3-ply | 10× less 3-ply | Full Tenso | 5× less Tenso | 10× less Tenso |
| Staphylococcus aureus ATCC 6538 | >10 | >10 | 6 | >10 | ~10 | >10 |
| Pseudomonas aeruginosa ATCC 9027 | >10 | ~10 | 5 | 4 | >10 | 4 |
| Klebsiella pneumoniae ATCC 4352 | >10 | >10 | >10 | >10 | >10 | >10 |
| Staphylococcus epidermidis ATCC 35984 | >10 | 9 | 9 | >10 | >10 | >10 |
| Candida albicans ATCC 18804 | >10 | >10 | >10 | >10 | >10 | 8 |

Conclusions

In general, using 5× less $Ag_5IO_6$ to coat dressings did not impact the number of days that zones of inhibition could be generated. However, for a few organisms, using 10× less $Ag_5IO_6$ in the coating process resulted in reduced longevity, suggesting that the dressings should be coated with at least that quantity of $Ag_5IO_6$ to obtain good bacteriostatic longevity.

Example 8—Efficacy at Various Concentrations and Comparison to Other Silver Dressings This study evaluated the antimicrobial activity (anti-adherence and effect on surrounding planktonic bacteria) of $Ag_5IO_6$ incorporated into two dressing types at three different concentrations against the 5 microorganisms used in Example 7, and compared the dressings to three commercially available silver-containing dressings.

Dressings
- A: Untreated 3-ply dressings (rayon/polyester core with upper and lower HDPE layers)—growth control for all B dressings below
- B Full: $Ag_5IO_6$ treated 3 ply dressings treated at full strength
- B-5×: $Ag_5IO_6$ treated 3 ply dressings treated at 5× less concentration
- B-10×: $Ag_5IO_6$ treated 3 ply dressings treated at 10× less concentration
- C: Untreated Tensoplast™ (cotton/rayon cloth with elastic adhesive)—growth control for all D dressings below
- D Full: $Ag_5IO_6$ treated 3 ply dressings treated at full strength
- D-5×: $Ag_5IO_6$ treated 3 ply dressings treated at 5× less concentration
- D-10×: $Ag_5IO_6$ treated 3 ply dressings treated at 10× less concentration
- E: Aquacel® (growth control for F)
- F: Aquacel® Ag
- G: Untreated 3-ply dressings wrapped around stainless steel (growth control for H)
- H: Acticoat*wrapped around stainless steel so that uncoated side was not exposed
- I: SeaSorb® (growth control for J)
- J: SeaSorb® Ag Methods A BEST™ assay used, with a challenge in 10% media+25% human serum in 0.9% saline-24 h biofilm growth. Both planktonic and adhered bacteria (biofilm) recovery performed.

Results

*Pseudomonas aeruginosa* ATCC 27853

| | Planktonic | | Adhered Biomass | |
| --- | --- | --- | --- | --- |
| Code | Log R (IC) | Log R (Control) | Log R (IC) | Log R (Control) |
| A | −3.35 | | −1.76 | |
| B Full | 5.00 | 8.65 | 3.80 | 5.83 |
| B - 5X | 5.00 | 8.65 | 5.00 | 7.16 |
| B - 10X | 5.00 | 8.65 | 5.00 | 7.16 |
| C | −3.54 | | −2.21 | |
| D Full | 5.00 | 8.84 | 5.00 | 7.61 |
| D - 5X | 5.00 | 8.84 | 5.00 | 7.61 |
| D - 10X | 5.00 | 8.84 | 5.00 | 7.61 |
| E | −2.00 | | −1.23 | |
| F | 5.00 | 7.30 | 5.00 | 6.63 |
| G | −0.88 | | −0.13 | |
| H | 3.43 | 4.58 | 5.00 | 5.60 |
| I | −3.10 | | −1.00 | |
| J | 5.00 | 8.40 | 5.00 | 6.40 |

*Staphylococcus epidermidis* ATCC 35984

| | Planktonic | | Adhered Biomass | |
| --- | --- | --- | --- | --- |
| Code | Log R (IC) | Log R (Control) | Log R (IC) | Log R (Control) |
| A | −2.86 | | −1.04 | |
| B Full | 5.26 | 8.42 | 5.26 | 6.70 |
| B - 5X | 5.26 | 8.42 | 5.26 | 6.70 |
| B - 10X | 2.71 | 5.66 | 4.26 | 5.57 |
| C | −2.72 | | −0.61 | |
| D Full | 5.42 | 8.44 | 5.42 | 6.42 |
| D - 5X | 4.12 | 7.04 | 5.42 | 6.42 |
| D - 10X | 3.22 | 6.04 | 5.42 | 6.42 |
| E | −2.94 | | −1.23 | |
| F | 4.31 | 7.45 | 5.26 | 6.89 |
| G | −3.62 | | −1.43 | |
| H | 2.41 | 6.16 | 2.93 | 4.52 |
| I | −3.59 | | −2.30 | |
| J | 4.49 | 8.29 | 3.36 | 5.93 |

*Staphylococcus aureus* ATCC 6538

| | Planktonic | | Adhered Biomass | |
| --- | --- | --- | --- | --- |
| Code | Log R (IC) | Log R (Control) | Log R (IC) | Log R (Control) |
| A | −2.14 | | −0.58 | |
| B Full | 4.73 | 7.07 | 5.59 | 6.57 |
| B - 5X | 5.59 | 8.04 | 5.59 | 6.57 |
| B - 10X | 1.68 | 3.92 | 2.44 | 3.15 |
| C | −1.43 | | 0.41 | |
| D Full | 5.67 | 7.40 | 5.67 | 5.66 |
| D - 5X | 5.67 | 7.40 | 5.67 | 5.66 |
| D - 10X | 5.67 | 7.40 | 5.67 | 5.66 |
| E | −1.64 | | −0.09 | |
| F | 4.39 | 6.23 | 5.59 | 6.08 |
| G | −1.63 | | −0.71 | |
| H | −1.49 | 0.14 | −0.84 | −0.13 |
| I | −1.71 | | −1.14 | |
| J | 5.59 | 7.60 | 5.59 | 7.13 |

*Klebsiella pneumoniae* ATCC 4352

| | Planktonic | | Adhered Biomass | |
| --- | --- | --- | --- | --- |
| Code | Log R (IC) | Log R (Control) | Log R (IC) | Log R (Control) |
| A | −3.83 | | −1.51 | |
| B Full | 5.49 | 9.62 | 5.49 | 7.40 |
| B - 5X | 5.49 | 9.62 | 5.49 | 7.40 |
| B - 10X | 3.41 | 7.33 | 4.67 | 6.44 |
| C | −3.48 | | −1.63 | |
| D Full | 5.52 | 9.30 | 5.52 | 7.55 |
| D - 5X | 5.52 | 9.30 | 5.52 | 7.55 |
| D - 10X | 5.52 | 9.30 | 3.95 | 5.71 |
| E | −3.59 | | −2.25 | |
| F | 4.54 | 8.33 | 5.49 | 8.14 |
| G | −3.50 | | −2.37 | |
| H | 3.84 | 7.60 | 4.39 | 7.08 |
| I | −3.77 | | −2.98 | |
| J | 5.49 | 9.56 | 5.49 | 8.88 |

*Candida albicans* ATCC 18804

| Coupon Code | Planktonic | | Adhered Biomass | |
|---|---|---|---|---|
| | Log R (IC) | Log R (Control) | Log R (IC) | Log R (Control) |
| A | −1.11 | | 0.69 | |
| B Full | 5.51 | 6.92 | 5.51 | 5.22 |
| B - 5X | 5.51 | 6.92 | 5.51 | 5.22 |
| B - 10X | 1.29 | 2.50 | 2.44 | 1.89 |
| C | −1.22 | | 0.56 | |
| D Full | 5.51 | 7.03 | 5.51 | 5.35 |
| D - 5X | −0.40 | 0.81 | 4.17 | 3.75 |
| D - 10X | 2.21 | 3.52 | 5.51 | 5.35 |
| E | −0.69 | | 0.86 | |
| F | 1.43 | 2.12 | 5.51 | 5.05 |
| G | −1.26 | | 0.11 | |
| H | 0.69 | 1.95 | 2.76 | 2.81 |
| I | −0.87 | | −0.05 | |
| J | 5.51 | 6.68 | 5.51 | 5.96 |

Statistical analyses were performed to compare the different test dressings (using the log reduction based on the control dressings) against planktonic bacteria and against bacterial adherence for each species. One-way ANOVAs were performed with Tukey-Kramer post-testing.

*Pseudomonas aeruginosa*

For the planktonic testing, there were significant differences between test dressings (p=0.0007), with B Full, B-5x, B-10x, D Full, D-5x, D-10x, and J all generating significantly greater log reductions than H ($p<0.01$ each).

For the adherence testing, there were significant differences between test dressings (p=0.0241), but the post testing did not identify any specific differences.

*Staphylococcus epidermidis*

For the planktonic testing, there were no significant differences between test dressings (p=0.4174).

For the adherence testing, there were no significant differences between test dressings (p=0.7263).

*Staphylococcus aureus*

For the planktonic testing, there were significant differences between test dressings (p=0.0001), with B Full, B-5x, D Full, D-5x, D-10x, and J all generating significantly greater log reductions than H ($p<0.001$ each). F also generated significantly greater log reductions than H ($p<0.01$).

For the adherence testing, there were significant differences between test dressings ($p<0.0001$), with B Full, B-5x, D Full, D-5x, D-10x, F, and J all generating significantly greater log reductions than H ($p<0.001$ each). As well, B Full, B-5x, and J generated significantly greater log reductions than B-10x ($p<0.05$ each). B-10x, however, did generate significantly greater log reductions than H ($p<0.05$).

*Klebsiella pneumoniae*

For the planktonic testing, there were no significant differences between test dressings (p=0.3528).

For the adherence testing, there were no significant differences between test dressings (p=0.0790).

*Candida albicans*

For the planktonic testing, there were significant differences between test dressings (p=0.0010), with B Full, B-5x, D Full, and J all generating significantly greater log reductions than D-5x ($p<0.05$ each).

For the adherence testing, there were significant differences between test dressings (p=0.0270), with B-10x generating significantly lower log reductions than J ($p<0.05$).

Conclusions

Overall, the results showed that the dressings with $Ag_5IO_6$ coating performed as well as or better than the commercial silver dressings at "full strength" coating. Typically, this was also true of the dressings with 5x and 10x less coating, but there were instances where they did not perform as well as Dressing J (SeaSorb Ag) in the adherence testing. This suggests that the 10x lower coating might be the limit in terms of how much the silver content of the dressings should be decreased.

Example 9—Efficacy after Saline Soaks and Comparison to Other Silver Dressings

This study compared $Ag_5IO_6$ coated dressings to uncoated controls and inoculum checks using a BEST™ assay. Commercial silver-containing dressings were also tested, along with their uncoated controls, for comparison. In this test, both the ability to prevent bacterial adherence/biofilm formation and the ability to kill surrounding planktonic bacteria were tested. In this study, dressings were pre-soaked in saline for 24 h, 7 days (3 saline changes), and 14 days (6 saline changes), to provide an idea of how the dressings would perform after exposure to the Cl⁻ present in wounds for various numbers of days. 3 organisms were tested. The challenge was performed in 10% media in 0.9% saline+25% human serum, again to determine how the dressings performed in the presence of bodily fluids, and the biofilms were allowed 24 h to grow.

Dressings Coated

A) Uncoated 3-ply dressing wrapped around stainless steel (rayon/polyester core with upper and lower HDPE layers)—control for B B) Acticoat*

C) Aquacel®—control for D

D) Aquacel® Ag

E) Uncoated 3-ply dressing—control for F

F) 3-ply dressings coated with $Ag_5IO_6$

G) Uncoated Tensoplast™ (cotton/rayon cloth bandage with elastic adhesive)—control for H H) Tensoplast™ coated with $Ag_5IO_6$ I) SeaSorb®—control for J J) SeaSorb® Ag Results Day 1

*Pseudomonas aeruginosa* ATCC 27853

| Coupon Code | Planktonic | | Adhered Biomass | |
|---|---|---|---|---|
| | Log R (IC) | Log R (Control) | Log R (IC) | Log R (Control) |
| A | −3.00 | | −2.20 | |
| B | 2.35 | 5.61 | 1.07 | 3.43 |
| C | −3.15 | | −2.19 | |
| D | 3.47 | 6.82 | 4.17 | 6.62 |
| E | −3.26 | | −2.42 | |
| F | 5.00 | 8.56 | 5.00 | 7.82 |
| G | −3.26 | | −1.10 | |
| H | 5.00 | 8.56 | 5.00 | 6.50 |
| I | −3.36 | | −2.26 | |
| J | 5.00 | 8.66 | 5.00 | 7.66 |

Staphylococcus aureus ATCC 6538

| Coupon Code | Planktonic Log R (IC) | Planktonic Log R (Control) | Adhered Biomass Log R (IC) | Adhered Biomass Log R (Control) |
|---|---|---|---|---|
| A | −2.25 | | −0.99 | |
| B | −0.71 | 1.53 | −0.45 | 0.53 |
| C | −1.50 | | −0.45 | |
| D | 2.01 | 3.51 | 2.35 | 2.93 |
| E | −1.66 | | −0.68 | |
| F | 5.32 | 7.28 | 5.32 | 6.39 |
| G | −0.18 | | 1.77 | |
| H | 5.30 | 5.78 | 5.30 | 3.93 |
| I | −1.94 | | −0.71 | |
| J | 4.42 | 6.56 | 5.32 | 6.42 |

Candida albicans ATCC 18804

| Coupon Code | Planktonic Log R (IC) | Planktonic Log R (Control) | Adhered Biomass Log R (IC) | Adhered Biomass Log R (Control) |
|---|---|---|---|---|
| A | −2.23 | | −0.90 | |
| B | −1.20 | 1.03 | −0.42 | 0.48 |
| C | −2.09 | | 0.60 | |
| D | −1.33 | 0.76 | 4.33 | 4.13 |
| E | −1.87 | | 0.49 | |
| F | 2.57 | 4.53 | 4.33 | 4.24 |
| G | −1.97 | | −0.09 | |
| H | 3.33 | 5.50 | 4.33 | 4.82 |
| I | −1.72 | | −1.03 | |
| J | −1.16 | 0.56 | 2.33 | 3.63 |

Day 7

Pseudomonas aeruginosa ATCC 27853

| Coupon Code | Planktonic Log R (IC) | Planktonic Log R (Control) | Adhered Biomass Log R (IC) | Adhered Biomass Log R (Control) |
|---|---|---|---|---|
| A | −2.32 | | −1.70 | |
| B | 5.30 | 8.02 | 5.30 | 7.48 |
| C | −2.51 | | −2.16 | |
| D | 4.40 | 7.11 | 5.30 | 7.86 |
| E | −2.84 | | −1.73 | |
| F | 3.97 | 7.01 | 4.47 | 6.47 |
| G | −2.76 | | −1.26 | |
| H | 5.30 | 8.36 | 5.30 | 6.96 |
| I | −2.96 | | −1.96 | |
| J | 5.30 | 8.56 | 5.30 | 7.66 |

Staphylococcus aureus ATCC 6538

| Coupon Code | Planktonic Log R (IC) | Planktonic Log R (Control) | Adhered Biomass Log R (IC) | Adhered Biomass Log R (Control) |
|---|---|---|---|---|
| A | −0.48 | | −0.33 | |
| B | −0.09 | 0.39 | −0.15 | 0.19 |
| C | 0.05 | | 0.93 | |
| D | 0.95 | 0.90 | 6.11 | 5.58 |
| E | 0.00 | | 0.85 | |
| F | 6.11 | 6.42 | 6.11 | 5.66 |
| G | 0.01 | | 1.60 | |
| H | 6.11 | 6.40 | 5.24 | 3.91 |
| I | −0.28 | | 0.11 | |
| J | 5.24 | 5.73 | 6.11 | 6.40 |

Candida albicans ATCC 18804

| Coupon Code | Planktonic Log R (IC) | Planktonic Log R (Control) | Adhered Biomass Log R (IC) | Adhered Biomass Log R (Control) |
|---|---|---|---|---|
| A | 0.96 | | 0.73 | |
| B | 0.19 | −0.77 | 0.41 | −0.31 |
| C | 0.44 | | 1.94 | |
| D | 0.73 | 0.29 | 5.26 | 3.72 |
| E | −0.10 | | 1.86 | |
| F | 5.26 | 5.66 | 5.26 | 3.80 |
| G | 1.70 | | 5.90 | |
| H | 4.18 | 2.58 | 5.90 | 0.00** |
| I | 1.70 | | 5.90 | |
| J | 4.18 | 2.58 | 5.90 | 0.00 |

**Note:
This data is because the *C. albicans* did not adhere to the uncoated test article on this day.

Day 14

Pseudomonas aeruginosa ATCC 27853

| Coupon Code | Planktonic Log R (IC) | Planktonic Log R (Control) | Adhered Biomass Log R (IC) | Adhered Biomass Log R (Control) |
|---|---|---|---|---|
| A | −3.36 | | −2.67 | |
| B | −1.49 | 1.87 | −0.95 | 1.72 |
| C | −3.20 | | −2.26 | |
| D | 3.77 | 7.17 | 3.87 | 6.39 |
| E | −3.20 | | −2.61 | |
| F | 5.20 | 8.70 | 2.07 | 4.68 |
| G | −3.00 | | −1.84 | |
| H | 5.20 | 8.50 | 5.20 | 7.44 |
| I | −3.29 | | −2.12 | |
| J | 5.20 | 8.79 | 2.61 | 4.86 |

Staphylococcus aureus ATCC 6538

| Coupon Code | Planktonic Log R (IC) | Planktonic Log R (Control) | Adhered Biomass Log R (IC) | Adhered Biomass Log R (Control) |
|---|---|---|---|---|
| A | −1.19 | | −0.33 | |
| B | −0.50 | 0.69 | 0.24 | 0.57 |
| C | −0.47 | | 0.19 | |
| D | 0.06 | 0.53 | 2.57 | 2.38 |
| E | −0.63 | | 0.70 | |
| F | 5.67 | 6.60 | 5.67 | 5.36 |
| G | −0.87 | | 0.90 | |
| H | 5.67 | 6.84 | 1.05 | 0.15 |
| I | −1.06 | | −0.39 | |
| J | 2.61 | 3.67 | 1.58 | 1.97 |

| | *Candida albicans* ATCC 18804 | | | |
|---|---|---|---|---|
| | Planktonic | | Adhered Biomass | |
| Coupon Code | Log R (IC) | Log R (Control) | Log R (IC) | Log R (Control) |
| A | −0.58 | | −0.74 | |
| B | −0.11 | 0.48 | 0.20 | 0.95 |
| C | −0.66 | | 0.66 | |
| D | −0.87 | −0.21 | 1.88 | 1.22 |
| E | −0.67 | | −0.12 | |
| F | 5.08 | 6.05 | 5.08 | 5.59 |
| G | −0.82 | | 0.66 | |
| H | 3.78 | 4.79 | 1.93 | 1.27 |
| I | −1.12 | | −0.78 | |
| J | −0.23 | 0.89 | 1.46 | 2.24 |

Statistical Analysis

Statistical analyses were performed for each pre-soak condition (1 day, 7 days, 14 days), for each organism (both planktonic and adhered), to compare the different silver-coated dressings. For the statistical analyses, log reductions calculated relative to the growth on the uncoated dressings were used, and one-way ANOVAs with Tukey-Kramer Multiple Comparison Post Tests were performed:

Day 1:
   *Pseudomonas aeruginosa* (planktonic): There were no significant differences between dressings (p=0.4987).
   *Staphylococcus aureus* (planktonic): There were significant differences between dressings (p=0.0005), with dressings F, H, and J generating significantly higher log reductions than dressing B (p<0.001, p<0.01, and p<0.01, respectively). As well, dressings F and J generated significantly higher log reductions than dressing D (p<0.05 each).
   *Candida albicans* (planktonic): There were significant differences between dressings (p=0.0009), with dressings B, D, and J generating significantly lower log reductions than F (p<0.05 each) and J (p<0.01 each).
   *Pseudomonas aeruginosa* (adhered): There were no significant differences between dressings (p=0.0896).
   *Staphylococcus aureus* (adhered): There were significant differences between dressings (p=0.0009), with dressings F and J generating significantly larger log reductions than dressings B (p<0.01 each) and D (p<0.05 each).
   *Candida albicans* (adhered): There were no significant differences between dressings (p=0.0614).

Day 7:
   *Pseudomonas aeruginosa* (planktonic): There were no significant differences between dressings (p=0.5326).
   *Staphylococcus aureus* (planktonic): There were significant differences between dressings (p<0.0001), with dressings F, H, and J generating significantly higher log reductions than dressings B and D (p<0.001 for each combination).
   *Candida albicans* (planktonic): There were significant differences between dressings (p<0.0001), with dressing F generating significantly higher log reductions than dressings B (p<0.001), D (p<0.001), H (p<0.01), and J (p<0.001). As well, dressing H generated significantly higher log reductions than dressings B (p<0.01), and D (p<0.05).
   *Pseudomonas aeruginosa* (adhered): There were no significant differences between dressings (p=0.2167).
   *Staphylococcus aureus* (adhered): There were significant differences between dressings (p<0.0001), with dressings D, F, H, and J generating significantly higher log reductions than dressing B (p<0.001, p<0.001, p<0.01, and p<0.001, respectively). As well, dressing H generated significantly higher log reductions than dressing J (p<0.05).
   *Candida albicans* (adhered): There were significant differences between dressings (p<0.0001), with dressing D generating significantly higher log reductions than dressings B and H (p<0.001 each). Dressing F generated significantly higher log reductions than dressing B (p<0.001), and H (p=0.001). Dressing H generated significantly higher log reductions than dressing B (p<0.05). Dressing J generated significantly higher log reductions than dressings B, D, F, and H (p<0.001). Note that on this day, the *C. albicans* did not adhere to the control dressing (G), for dressing H, making generation of a log reduction impossible.

Day 14:
   *Pseudomonas aeruginosa* (planktonic): There were significant differences between dressings (p=0.0003), with dressings D, F, H, and J generating significantly higher log reductions than dressing B (p<0.01, p<0.001, p<0.001, and p<0.001, respectively).
   *Staphylococcus aureus* (planktonic): There were significant differences between dressings (p<0.0001), with dressings F, J, and H generating significantly larger log reductions than dressings B and D (p<0.001, for each combination). As well, dressings F and H generated significantly larger log reductions than dressing J (p<0.001 each).
   *Candida albicans* (planktonic): There were significant differences between dressings (p=0.0001), with dressing F generating significantly larger log reductions than dressings B, D, and J (p<0.001, p<0.001, and p<0.01, respective). Dressing H also generated significantly larger log reductions than dressings B, D, and J (p<0.01, p<0.01, and p<0.05, respectively).
   *Pseudomonas aeruginosa* (adhered): There were significant differences between dressings (p=0.0253), with dressing H generating significantly higher log reductions than dressing B (p<0.05).
   *Staphylococcus aureus* (adhered): There were significant differences between dressings (p<0.0001), with dressing F generating significantly higher log reductions than dressings B, D, H and J (p<0.001 each). Dressing J generated significantly higher log reductions than dressings B and H (p<0.01, p<0.001, respectively). Dressing D generated significantly higher log reductions than dressings B and H (p<0.001).
   *Candida albicans* (adhered): There were significant differences between dressings (p<0.0001), with dressing F generating significantly higher log reductions than dressings B, D, H, and J (p<0.001 each). Dressing J also generated significantly higher log reductions than dressings B, D, and H (p<0.01, p<0.05, and p<0.05, respectively).

Conclusions

Overall, the $Ag_5IO_6$-coated dressings (F and H) performed well against all three organisms (gram positive, gram negative, and yeast), and demonstrated both anti-adherence and anti-planktonic activity. Even after 14 days exposure to saline, the dressings demonstrated bactericidal activity and anti-adherence properties under most conditions.

Where there were significant differences, the $Ag_5IO_6$-coated dressings out-performed the other dressings (with the exception of dressing J performing better than dressing H for adhered *S. aureus* and *C. albicans* at Day 14 only).

Example 10—$Ag_5IO_6$ Solubility in Water and Saline

The purpose of this study was to develop a basic understanding of the solubility (and stability) of $Ag_5IO_6$ in pure water and 0.9% (physiological saline), following OECD Method (105)—flask.

Methods:
1. About 0.1 g $Ag_5IO_6$ was weighed into 6 100 mL volumetric flasks.
2. The flasks were filled to volume with $ddH_2O$ or 0.9% saline.
3. The vessels were tightly stoppered and then agitated using a shaker in an incubator at 30° C. for approximately 24 hours.
4. After 24 hours, two of the vessels (one per solvent) were equilibrated for 24 h at the test temperature (20° C., using a water bath) with occasional shaking.
5. Pictures were obtained of the solutions and solid present.
6. The contents of the vessels were then centrifuged at the test temperature (20° C.).
7. The concentration of the test substance in the clear aqueous phase was determined by atomic absorption spectroscopy.
8. The pH of the solution was measured using a pH meter.
9. Triplicate samples of the solution were analyzed by UV-Vis spectroscopy.
10. A sample of the solid material was collected by vacuum filtration, allowed to dry on the filter for 15 minutes, then transferred to a watch glass and placed in the fume hood to dry overnight. The sample was then packaged in a glass vial covered in aluminum foil and submitted for XRD analysis.
11. The procedures of steps 4-10 were repeated for the second and third flask, after an initial equilibration at 30° C. for two and three days, respectively.

Results

The solubility of $Ag_5IO_6$ is much lower in saline (0.61±0.05 mg/L) than in $ddH_2O$ (24.41±0.87 mg/L). This is likely due to a combination of reaction with the $Cl^-$ and overall ionic strength in the solution reducing the amount of $Ag_5IO_6$ dissolvable. Note that the solubilities were calculated assuming that all Ag in solution is due to $Ag_5IO_6$, which was not the case.

The pH in saline (10) was consistently higher than the pH in $ddH_2O$ (8). The solids in the presence of saline were a lighter brown than the solids in $ddH_2O$.

While the UV-Vis spectra for the solutions in $ddH_2O$ and saline had one peak in common at ~206-212 nm, there was a shoulder at ~196-200 nm that was only present in the $ddH_2O$ sample, indicating some reaction of the $Ag_5IO_6$ with the saline. However the spectrum for $Ag_5IO_6$ in saline did not match that for AgCl.

The XRD data indicated that in saline, approximately 25% of the solid material collected at the end of the experiment was converted to AgCl, with the remainder as unreacted $Ag_5IO_6$. In $ddH_2O$, approximately 99.9% of the solid material remained as $Ag_5IO_6$ with 0.1% being converted to Ag metal.

Conclusions

The change in color of the solids in the presence of NaCl indicated that $Ag_5IO_6$ is somewhat unstable in a saline medium. This was confirmed by the XRD, which indicated some AgCl formation. The pH increase observed in saline solution suggested that when the silver in $Ag_5IO_6$, which is sequestered in $Ag_2O_6$ octahedra (highly oxidized), is converted to AgCl, the silver is reduced and water is oxidized resulting in the observed increase in pH. It is interesting to note that although there was 21× excess chloride ions available to react with the silver, only 25% of the silver was converted to silver chloride. This suggests that not all $Ag_5IO_6$ is converted to AgCl instantaneously, as occurs with many compounds (further confirmed by the fact that the UV-Vis spectra for $Ag_5IO_6$ in NaCl did not match the spectra for AgCl, suggesting that not all the silver species measured in solution were associated with AgCl). This result suggests that chloride-rich environments (e.g. wounds) may reduce the product's effectiveness to some extent, but that perhaps the AgCl formation is in some way self-limited or reduced relative to many silver compounds that are immediately converted to AgCl, indicating that $Ag_5IO_6$ may have advantages over such products. It is interesting to note that in the absence of saline (in pure $ddH_2O$), a very small portion of $Ag_5IO_6$ is reduced to metallic silver, but overall the $Ag_5IO_6$ appears to be relatively stable in $ddH_2O$.

The silver content results (no significant differences between days) and XRD data were very consistent from Days 1 through 3, indicating that the solubility limit of $Ag_5IO_6$ was obtained by Day 1.

Example 11—$Ag_5IO_6$ Stability in Solvents

The purpose of this study was to determine whether or not $Ag_5IO_6$ interacts with methanol, tetrahydrofuran, acetone, and acetonitrile.

Methods:
i. 2-3 mm of $Ag_5IO_6$ was placed in a vial, 2 mL of the solvent was added, and the vial was placed in a TAM III for an isothermal run at room temperature for >24 h with solvent only as the reference. The heat flow was measured.
ii. After the run was complete, the solvents were allowed to flash off and the solids collected were submitted to XRD.
iii. Samples exposed following essentially the same method for only 18 h were also submitted for XRD.

Results and Conclusions $Ag_5IO_6$ can be blended with all solvents for <18 h without substantial reaction at room temperature. Acetone is the first to show significant reaction (onset ~14 h-18 h), followed by methanol (onset ~33 h), then THF (onset ~56 h), then acetonitrile (slower onset at ~56 h). In terms of the solubility of $Ag_5IO_6$ in different organic solvents, methanol>>THF>acetone>acetonitrile. XRD results Example 12—$Ag_5IO_6$ Thermal/Storage Stability The purpose of this study was to determine the stability of $Ag_5IO_6$ at various temperatures independent of hydrolytic or photolytic effects, in order to obtain an understanding of its storage stability, and also to perform differential scanning calorimetry and thermal gravimetry.

Methods:
i. $Ag_5IO_6$ was made fresh, a sample was submitted for XRD analysis (Day 0), and then additional samples were placed at room temperature, 40° C., 54° C., and 90° C. for 14 and 28 days in amber glass vials placed in $CO_2$ impermeable foil pouches with desiccant packs. After the allotted time period, the samples were submitted for XRD.

Samples were submitted for DSC/TGA to measure thermal stability.

Results and Conclusions

Storage Stability:

Even at 90° C., at 14 and 28 days, grain growth occurred (from 14 Å at Day 0, to 62 Å at Day 14, to 94 Å at Day 28) but no compositional change was observed (the material remained 100% $Ag_5IO_6$).

Since stability at 54° C. for 28 days suggests a shelf life of >2 years at room temperature, this data demonstrates very good storage stability of $Ag_5IO_6$. The $Ag_5IO_6$ had a relatively high water content as-made (137370 ppm), indicating that even relatively "wet" product as dried using the current drying technique has very good storage stability.

With DSC and TGA analysis, there was an initial peak occurring between 50° C. and 106° C., which corresponded to grain growth, loss of adsorbed gases, and loss of adsorbed water. A second peak, which started at 442° C., corresponded to decomposition of the $Ag_5IO_6$. Thus, $Ag_5IO_6$ is stable past 400° C., indicating that it can be put through the thermal processing required to generate some medical devices without decomposition, although the grain size may increase.

Example 13—$Ag_5IO_6$ Photostability

The purpose of this study was to assess the photostability of $Ag_5IO_6$ in accordance with the FDA's 1997 recommendations regarding the photostability testing of new products.

Methods:

$Ag_5IO_6$ was ground, spread thinly on watch glasses, protected from foreign objects, and, along with aluminum foil covered controls, the watch glasses were placed face up under cool-light metal halide lamps such that the samples were receiving at least 700 fc, and the lux exposure was measured regularly until greater than 1.3 million lux hours exposure had occurred. The samples were then submitted for XRD.

Results and Conclusions

After greater than 1.3 million lux hours exposure, the material was still 100% $Ag_5IO_6$. $Ag_5IO_6$ has very good photostability and does not need to be stored protected from light.

Example 14—Efficacy Against *C. difficile*

This study compared $Ag_5IO_6$ coated dressings to uncoated controls and inoculum checks using a BEST™ assay. Commercial silver-containing dressings were also tested, along with their uncoated controls, for comparison. In this test, both the ability to prevent *Clostridium difficile* adherence/biofilm formation and the ability to kill surrounding planktonic *Clostridium difficile* were tested. The challenge was performed in 10% media in 0.9% saline+25% human serum, to determine how the dressings performed in the presence of bodily fluids, and the biofilms were allowed 24 h to grow.

Dressings Coated
 A) Uncoated 3-ply dressing—control for B
 B) 3-ply dressings coated with $Ag_5IO_6$
 C) Uncoated Tensoplast™ (cotton/rayon cloth bandage with elastic adhesive)—control for D
 D) Tensoplast™ coated with $Ag_5IO_6$
 E) SeaSorb®—control for F
 F) SeaSorb® Ag
 G) Aquacel®—control for H
 H) Aquacel® Ag Results

| | *Clostridium difficile* ATCC 9689 | | | |
|---|---|---|---|---|
| | Planktonic | | Adhered Biomass | |
| Coupon Code | Log R (IC) | Log R (Control) | Log R (IC) | Log R (Control) |
| A | −2.95 | | −1.00 | |
| B | −2.87 | 0.07 | −1.06 | −0.06 |
| C | −2.53 | | −0.83 | |
| D | 0.80 | 3.37 | 2.06 | 2.88 |
| E | −2.69 | | −1.78 | |
| F | −2.98 | −0.29 | −1.93 | −0.14 |
| G | −2.87 | | −1.87 | |
| H | −2.71 | 0.16 | −1.74 | 0.13 |

Statistical Analysis

Statistical analyses were performed for both planktonic and adhered data, to compare the different silver-coated dressings. For the statistical analyses, log reductions calculated relative to the growth on the uncoated dressings were used, and one-way ANOVAs with Tukey-Kramer Multiple Comparison Post Tests were performed:

Planktonic: There were significant differences between dressings (p<0.0001), with Dressing B generating significantly higher log reductions than Dressings D, F, and H (p<0.001 each).

Adhered: There were significant differences between dressings (p<0.0001), with Dressing B generating significantly higher log reductions than Dressings D, F, and H (p<0.001 each).

Conclusions

Overall, only the $Ag_5IO_6$-coated 3-ply dressings demonstrated activity against *C. difficile*, both killing the planktonic bacteria and preventing adherence with log reductions>3, and just under 3, respectively. This indicates that $Ag_5IO_6$ may be an effective agent against *C. difficile* in appropriate formulations, where other commercial silver-containing dressings were not.

Example 15—Diabetic and Normal Pig Wound Healing

In this study, diabetic pigs were generated, and then wounds were created on both the diabetic and normal pigs, and either $Ag_5IO_6$-coated gauze or uncoated gauze were used to treat the wounds.

Methods
  6 test animals were used (3 normal pigs, 3 diabetic pigs)
  Diabetes was generated in pigs (Alloxan monohydrate, 175 mg/kg in 0.9% saline, pH 7.0, ~50 mL per pig, infused into pig ear vein; normal pigs received 50 mL 0.9% saline, pH 7.0 by the same method).
  Porcine full thickness wounds were generated.
  Test wounds on normal and diabetic pigs were treated with $Ag_5IO_6$-coated 100% cotton sponge gauze; control wounds on normal and diabetic pigs were treated with uncoated gauze.
  Bandages were covered with Opsite* and secured with Elastoplast. Bandages were changed 2x/week.
  Sampling occurred on Days 0, 3, 7, 15, and 21, with 4 samples taken per animal per day: Sterile swabs were pre-wetted in sterile 0.9% saline/PBS, gently swabbed over the bandage site and then swabbed over the corresponding wound site. The swabs were placed in neutralizer and then the neutralizer was sonicated, serially diluted, and spot plated. Wound sizes were measured, and wound redness (erythema) and swelling (edema) were scored on a scale from 0 (no swelling/redness) to 4 (extremely swollen/red).

Conclusions

There was a significant reduction of bacteria with the test dressing in both the normal and diabetic pigs at Days 3 and 7.

In the diabetic pigs, there was a reduction in redness with the test dressing relative to the control dressings. With the normal pigs, the redness score was lower on the test dressings relative to the control dressings on Day 3 and similar on other days.

In the diabetic pigs, the swelling score was higher with the test dressings up to Day 15, but then was the same as the control dressings. In the normal pigs, the swelling score was consistently somewhat higher in the test dressings than in the control dressings.

In the diabetic pigs, the wound sizes were larger for the test dressing than for the control dressing at Day 7, the wound sizes were similar at Day 15, and the wound sizes for the test dressing were substantially smaller than the wound sizes for the control dressing at Day 21. A similar pattern was observed for the normal pigs.

Overall, the test dressings reducing initial bacterial load, did not substantially irritate the wounds (as would be indicated by swelling and redness), and promoted wound size reduction.

Example 16—Bean Test with Soil Pre-Soak

In this study, the antimicrobial properties of various silver-coated seeds, after exposure to soil, were tested using a carrier test in a BEST™ Assay device. ddH$_2$O rinsed and UV-sterilized pinto beans were coated with AgO, AgNO$_3$, or Ag$_5$IO$_6$ using solutions or slurries at 4 different equivalent total silver concentrations (denoted 100×, 10×, 1×, and 0.1×). Uncoated seeds were used for growth controls and sterility controls.

Test organisms: *Pseudomonas syringae* pv. *syringae*; *Pseudomonas syringae* pv. *phaseolicola*; *Curtobacterium flaccumfaciens* pv. *flaccumfaciens*.

The coated seeds were attached to a bacterial growth and challenge device, placed for 2 hours in wet soil to determine whether the soil would inactivate the coatings, and then the soil was briefly rinsed off the beans with sterile water, and they were inoculated by placing them in full strength inoculum for 10 minutes, followed by a 1 h incubation period over empty-welled plates in a moist environment to allow the bacteria time to adhere. The beans were then placed in ddH$_2$O for a 0.5 h challenge, and then placed in neutralizer, sonicated, serially diluted, and spot plated. Log reductions were calculated both relative to the original inoculum and relative to the control (uncoated beans).

Results

Log Reductions

| | Average Log$_{10}$ Reduction | | | | | |
|---|---|---|---|---|---|---|
| | *P. syringae* pv. *syringae* | | *P. syringae* pv. *phaseolicola* | | *C. flaccumfaciens* pv. *flaccumfaciens* | |
| Sample Code | LogR (IC) | LogR (C) | LogR (IC) | LogR (C) | LogR (IC) | LogR (C) |
| AgO-100 | 8.01 | 5.38 | 8.56 | 5.97 | 4.06 | 1.21 |
| AgO-10 | 6.94 | 3.98 | 7.81 | 5.05 | 3.83 | 0.98 |
| AgO-1 | 3.74 | 0.45 | 3.41 | 0.16 | 4.25 | 1.40 |
| AgO-0.1 | 3.22 | −0.07 | 3.41 | 0.15 | 4.06 | 1.21 |

| | Average Log$_{10}$ Reduction | | | | | |
|---|---|---|---|---|---|---|
| | *P. syringae* pv. *syringae* | | *P. syringae* pv. *phaseolicola* | | *C. flaccumfaciens* pv. *flaccumfaciens* | |
| Sample Code | LogR (IC) | LogR (C) | LogR (IC) | LogR (C) | LogR (IC) | LogR (C) |
| AgNO$_3$-100 | 7.51 | 4.72 | 7.62 | 4.86 | 3.71 | 0.86 |
| AgNO$_3$-10 | 4.80 | 1.51 | 5.32 | 2.07 | 3.38 | 0.53 |
| AgNO$_3$-1 | 3.18 | −0.11 | 3.99 | 0.74 | 3.38 | 0.53 |
| AgNO$_3$-0.1 | 2.29 | −1.00 | 3.29 | 0.04 | 3.88 | 1.03 |
| Ag$_5$IO$_6$-100 | 8.01 | 5.38 | 8.56 | 5.97 | 4.96 | 2.11 |
| Ag$_5$IO$_6$-10 | 6.46 | 3.50 | 8.06 | 5.30 | 3.38 | 0.53 |
| Ag$_5$IO$_6$-1 | 4.56 | 1.27 | 5.10 | 1.85 | 3.60 | 0.75 |
| Ag$_5$IO$_6$-0.1 | 2.75 | −0.54 | 4.73 | 1.48 | 3.43 | 0.58 |

Statistical Analysis:

One-way ANOVAs with Tukey-Kramer multiple comparisons post tests were also performed to compare the different silver compounds at each concentration with each microorganism. The log reductions calculated compared to the growth control (uncoated) beans were used for the analysis.

*Pseudomonas syringae* pv. *syringae*
  100×, 10×, and 0.1× concentrations: There were no significant differences between bean coatings (p=0.4053, p=0.1192, and p=0.2367, respectively).
  1× concentration: There were significant differences between bean coatings (p=0.0207), with the Ag$_5$IO$_6$ generating a higher log reduction than the AgNO$_3$ (p<0.05).

*Pseudomonas syringae* pv. *phaseolicola*
  100× concentration: There were no significant differences between bean coatings (p=0.4053).
  10× concentration: There were significant differences between bean coatings (p=0.0123), with the AgO and Ag$_5$IO$_6$ generating significantly larger log reductions than the AgNO$_3$ (p<0.05 each).
  1× concentration: There were significant differences between bean coatings (p=0.0105), with the Ag$_5$IO$_6$ generating significantly larger log reductions than the AgO (p<0.01).
  0.1× concentration: There were significant differences between bean coatings (p=0.0299), with the Ag$_5$IO$_6$ generating significantly larger log reductions than the AgNO$_3$ (p<0.05).

*Curtobacterium flaccumfaciens* pv. *flaccumfaciens*
  100× concentration: There were significant differences between bean coatings (p=0.0328), with Ag$_5$IO$_6$ generating significantly larger log reductions than AgNO$_3$ (p<0.05).
  10× and 0.1× concentrations: There were no significant differences between bean coatings (p=0.3589, and p=0.1038, respectively).
  1× concentration: There were significant differences between bean coatings (p=0.0257), with the AgO generating significantly larger log reductions than AgNO$_3$ (p<0.05).

Conclusions

Overall, the coatings tended to be more effective at 100× and 10× concentration than at 1× or 0.1× concentrations.

Overall, where there were significant differences, the Ag$_5$IO$_6$ coated beans tended to perform better than the other bean coatings.

Overall, at the higher concentrations, all bean coatings were able to survive 2 h in soil and still prevent adherence to the beans in the biofilm test. However, at lower concentrations, the effect was much less.

The $Ag_5IO_6$ coated beans demonstrated the best performance in this study, with better activity than silver nitrate, and similar activity to AgO, in terms of higher kill rates at a given concentration, and activity at lower concentrations.

All the coatings were more active against the *Pseudomonas* strains than against the *Curtobacterium* strain.

While the invention has been described in some detail by way of illustration and example, it should be understood that the invention is susceptible to various modifications and alternative forms, and is not restricted to the specific embodiments set forth in the Examples. It should be understood that these specific embodiments are not intended to limit the invention but, on the contrary, the intention is to cover all modifications, equivalents, and alternatives falling within the spirit and scope of the invention.

The invention claimed is:

1. An article of manufacture comprising one or more antimicrobial compounds that release an anion of $3^-$ charge containing both silver and orthoperiodate, selected from the group consisting of pentasilver hexaoxoiodate (formula, $Ag_5IO_6$); $Ag_xH_yIO_6$, where x is a value between 1 and 5, and y is the corresponding value between 0 and 4 necessary to achieve the correct total positive charge of 5; $Ag_xM_yIO_6$ where x is a value between 1 and 5, y is a corresponding value between 0 and 4 necessary to achieve the correct total positive charge of 5, and M is one or more metals or hydrogen and combinations thereof; and combinations thereof; wherein $Ag_2H_3IO_6$ is excluded; and wherein the article of manufacture is selected from the group consisting of catheters; cannulae; needles; stents; guide wires; implant devices; filters; endoscopes; surgical or medical instruments; coils; contact lenses; IUDs; peristaltic pump chambers; endotracheal tubes; gastroenteric feeding tubes; arteriovenous shunts; condoms; oxygenator and kidney membranes; gloves; pacemaker leads; wound dressings; metallic pins, plates and screws; metallic artificial hips; artificial knees; and gels, creams, and ointments.

2. The article of manufacture of claim 1 wherein M is selected from the group consisting of K, Na, Mg, Ca, Au, Pt, Cu, Zn, H, and Fe, and combinations thereof.

3. The article of manufacture of claim 1 wherein the antimicrobial compound is $Ag_5IO_6$.

4. The article of manufacture of claim 1 wherein the antimicrobial compound comprises an anion selected from the group consisting of $Ag_2IO_6^{3-}$ and $AgMIO_6^{3-}$; and also comprises a cation selected from the group consisting of $Ag_3^{3+}$, $Ag_2M^{3+}$, $AgM^{3+}$, and $M^{3+}$, wherein M is one or more metals or hydrogen; and combinations thereof.

5. The antimicrobial compound of claim 4 wherein the M in $AgMIO_6^{3-}$ is selected from the group consisting of K, Na, Au, Cu, H, and Fe, and combinations thereof; and the M in $Ag_2M^{3+}$, $AgM^{3+}$, or $M^{3+}$ is selected from the group consisting of K, Na, Mg, Ca, Au, Pt, Cu, Zn, H, and Fe, and combinations thereof.

6. The article of manufacture of claim 1 wherein silver is present in both the anion and the cation.

7. A method of preventing or reducing microbial contamination on a substrate comprising coating a substrate with one or more silver (I) periodates antimicrobial compounds that release an anion of $3^-$ charge containing both silver and orthoperiodate, selected from the group consisting of pentasilver hexaoxoiodate (formula, $Ag_5IO_6$); $Ag_xH_yIO_6$, where x is a value between 1 and 5, and y is the corresponding value between 0 and 4 necessary to achieve the correct total positive charge of 5; $Ag_xM_yIO_6$ where x is a value between 1 and 5, y is a corresponding value between 0 and 4 necessary to achieve the correct total positive charge of 5, and M is one or more metals or hydrogen and combinations thereof; and combinations thereof; wherein $Ag_2H_3IO_6$ is excluded; and wherein the substrate is a wound dressing, a medical instrument, a medical device, a plant, a seed, or a portion thereof; and wherein the medical device is selected from the group consisting of catheters; cannulae; needles; stents; guide wires; implant devices; filters; endoscopes; surgical or medical instruments; coils; contact lenses; IUDs; peristaltic pump chambers; endotracheal tubes; gastroenteric feeding tubes; arteriovenous shunts; condoms; oxygenator and kidney membranes; gloves; pacemaker leads; metallic pins, plates, and screws; metallic artificial hips; and artificial knees.

8. The method of claim 7 wherein M is selected from the group consisting of K, Na, Mg, Ca, Au, Pt, Cu, Zn, H, and Fe, and combinations thereof.

9. The method of preventing or reducing microbial contamination on a substrate of claim 7 wherein the antimicrobial compound comprises an anion selected from the group consisting of $Ag_2IO_6^{3-}$ and $AgMIO_6^{3-}$; and also comprises a cation selected from the group consisting of $Ag_3^{3+}$, $Ag_2M^{3+}$, $AgM^{3+}$, and $M^{3+}$, wherein M is one or more metals or hydrogen; and combinations thereof.

10. The antimicrobial compound of claim 9 wherein the M in $AgMIO_6^{3-}$ is selected from the group consisting of K, Na, Au, Cu, H, and Fe, and combinations thereof; and the M in $Ag_2M^{3+}$, $AgM^{3+}$, or $M^{3+}$ is selected from the group consisting of K, Na, Mg, Ca, Au, Pt, Cu, Zn, H, and Fe, and combinations thereof.

11. An antimicrobial wound dressing comprising an antimicrobial coating containing one or more antimicrobial compounds that release an anion of $3^-$ charge containing both silver and orthoperiodate, selected from the group consisting of pentasilver hexaoxoiodate (formula, $Ag_5IO_6$); silver orthoperiodate; $Ag_2H_3IO_6$; $Ag_xH_yIO_6$, where x is a value between 1 and 5, and y is the corresponding value between 0 and 4 necessary to achieve the correct total positive charge of 5; $Ag_xM_yIO_6$, where x is a value between 1 and 5, y is the corresponding value between 0 and 4 necessary to achieve the correct total positive charge of 5, and M is one or more metals or hydrogen; and combinations thereof.

12. The wound dressing of claim 11 wherein one or more of the compounds are coated onto a wound dressing fiber.

13. The wound dressing of claim 11 wherein M is selected from the group consisting of K, Na, Mg, Ca, Au, Pt, Cu, Zn, H, and Fe, and combinations thereof.

14. The antimicrobial wound dressing of claim 11 wherein the antimicrobial coating comprises an anion selected from the group consisting of $Ag_2IO_6^{3-}$ and $AgMIO_6^{3-}$; and also comprises a cation selected from the group consisting of $Ag_3^{3+}$, $Ag_2M^{3+}$, $AgM^{3+}$, and $M^{3+}$, wherein M is one or more metals or hydrogen; and combinations thereof.

15. The antimicrobial coating of claim 14 wherein the M in $AgMIO_6^{3-}$ is selected from the group consisting of K, Na, Au, Cu, H, and Fe, and combinations thereof; and the M in $Ag_2M^{3+}$, $AgM^{3+}$, or $M^{3+}$ is selected from the group consisting of K, Na, Mg, Ca, Au, Pt, Cu, Zn, H, and Fe, and combinations thereof.

* * * * *